US00PP20676P2

(12) United States Plant Patent
van der Knaap

(10) Patent No.: US PP20,676 P2
(45) Date of Patent: Jan. 26, 2010

(54) ***ANTHURIUM* PLANT NAMED 'BARDONTA'**
(50) Latin Name: *Anthurium andreanum*
Varietal Denomination: Bardonta

(75) Inventor: Leonardus Johannus Maria van der Knaap, Naaldwijk (NL)

(73) Assignee: Knaap Licenties B.V., Naaldwijk (NL)

( * ) Notice: Subject to any disclaimer, the term of this patent is extended or adjusted under 35 U.S.C. 154(b) by 0 days.

(21) Appl. No.: 12/287,359

(22) Filed: Oct. 8, 2008

(51) Int. Cl.
*A01H 5/00* (2006.01)

(52) U.S. Cl. ..... Plt./365
(58) Field of Classification Search ..... Plt./365
See application file for complete search history.

*Primary Examiner*—Kent L Bell
(74) *Attorney, Agent, or Firm*—C. A. Whealy

(57) ABSTRACT

A new and distinct cultivar of *Anthurium* plant named 'Bardonta', characterized by its upright, outwardly arching and uniform plant habit; freely clumping growth habit; bushy and dense plants; glossy medium green-colored leaves; large red-colored spathes that are positioned above and beyond the foliage on strong and erect scapes; freely flowering habit; and good inflorescence longevity.

2 Drawing Sheets

Botanical designation: *Anthurium andreanum.*
Cultivar denomination: 'Bardonta'.

BACKGROUND OF THE INVENTION

The present invention relates to a new and distinct cultivar of *Anthurium* plant, botanically known as *Anthurium andreanum* and hereinafter referred to by the name 'Bardonta'.

The new *Anthurium* plant is a product of a controlled breeding program conducted by the Inventor in Maasland, The Netherlands. The objective of the breeding program is to create new *Anthuriums* that have uniform plant habit, good container performance and attractive foliage and inflorescence coloration.

The new *Anthurium* plant originated from a cross-pollination made by the Inventor on May 29, 2002, in Maasland, The Netherlands of a proprietary selection of *Anthurium andreanum* identified as code number 20013108-311, not patented, as the female, or seed, parent with a proprietary selection of *Anthurium andreanum* identified as code number 20009009-660, not patented, as the male, or pollen, parent. The new *Anthurium* was discovered and selected by the Inventor as a single flowering plant within the progeny of the stated cross-pollination in a controlled greenhouse environment in Maasland, The Netherlands on Jan. 13, 2004.

Asexual reproduction of the new *Anthurium* plant by tissue culture in a controlled environment in Lochristi, Belgium since Feb. 3, 2004 has shown that the unique features of this new *Anthurium* are stable and reproduced true to type in successive generations of asexual reproduction.

SUMMARY OF THE INVENTION

Plants of the new *Anthurium* have not been observed under all possible environmental conditions. The phenotype may vary somewhat with variations in environment such as temperature and light intensity, without, however, any variance in genotype.

The following traits have been repeatedly observed and are determined to be the unique characteristics of 'Bardonta'.

These characteristics in combination distinguish 'Bardonta' as a new and distinct cultivar of *Anthurium:*

1. Upright, outwardly arching and uniform plant habit.
2. Freely clumping growth habit; bushy and dense plants.
3. Glossy medium green-colored leaves.
4. Large red-colored spathes that are positioned above and beyond the foliage on strong and erect scapes.
5. Freely flowering habit.
6. Good inflorescence longevity.

Plants of the new *Anthurium* differ from plants of the female parent selection in the following characteristics:

1 . Plants of the new *Anthurium* are more freely branching than plants of the female parent selection.
2. Plants of the new *Anthurium* have larger spathes than plants of the female parent selection.
3. Plants of the new *Anthurium* and the female parent selection differ in spathe color as plants of the female parent selection have orange red-colored spathes with green-colored margins.

Plants of the new *Anthurium* differ from plants of the male parent selection in the following characteristics:

1. Plants of the new *Anthurium* have lighter green-colored leaves than plants of the male parent selection.
2. Plants of the new *Anthurium* have thicker stems than plants of the male parent selection.
3. Plants of the new *Anthurium* have larger spathes than plants of the male parent selection.

Plants of the new *Anthurium* can also be compared to plants of *Anthurium andreanum* 'Barmodu', disclosed in U.S. Plant Pat. No. 18,844. In side-by-side comparisons conducted in Maasland, The Netherlands, plants of the new *Anthurium* differed from plants of 'Barmodu' in the following characteristics:

1. Plants of the new *Anthurium* were more vigorous than plants of 'Barmodu'.
2. Inflorescences of plants of the new *Anthurium* were positioned higher above the foliar plane than inflorescences of plants of 'Barmodu'.
3. Plants of the new *Anthurium* and 'Barmodu' differed in inflorescence color as plants of 'Barmodu' had dark pink-colored spathes and lilac purple-colored spadices.

BRIEF DESCRIPTION OF THE PHOTOGRAPHS

The accompanying photographs illustrate the overall appearance of the new *Anthurium*. These photographs show the colors as true as it is reasonably possible to obtain in colored reproductions of this type. Colors in the photographs may differ slightly from the color values cited in the detailed botanical description which accurately describe the colors of the new *Anthurium*.

The photograph on the first sheet is a side perspective view of a typical plant of 'Bardonta' grown in a container.

The photograph on the second sheet is a close-up view of a typical inflorescence of 'Bardonta'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown in 17-cm containers in Maasland, The Netherlands during the summer in a glass-covered greenhouse. Plants were grown under conditions and practices which approximate those generally used in commercial *Anthurium* production. During the production of the plants, day temperatures ranged from about 19° C. to 24° C., night temperatures ranged from about 19° C. to 22° C. and light levels were about 10,000 lux. Plants had been growing for 45 weeks when the photographs and the detailed description were taken.

Botanical classification: *Anthurium andreanum* 'Bardonta'.

Parentage:

*Female, or seed, parent.*—Proprietary selection of *Anthurium andreanum* identified as code number 20013108-311, not patented.

*Male, or pollen, parent.*—Proprietary selection of *Anthurium andreanum* identified as code number 20009009-660, not patented.

Propagation:

*Type.*—By tissue culture.

*Time to initiate roots.*—About ten days at 23° C.

*Time to produce a rooted young plant.*—About 180 to 200 days at 21° C.

*Root description.*—Medium in thickness, fibrous; white in color.

*Rooting habit.*—Moderately branching, moderately dense.

Plant description:

*Plant shape.*—Upright and outwardly spreading plant habit; inverted triangle; symmetrical.

*Growth habit.*—Freely clumping, bushy and dense growth habit; about 14 clumps develop per plant; moderately vigorous.

*Plant height, from soil level to top of leaf plane.*—About 37.8 cm.

*Plant height, from soil level to top of inflorescences.*—About 48.7 cm.

*Plant diameter or spread.*—About 54.6 cm.

*Foliage description.*—Arrangement: Alternate; simple. Length: About 13.7 cm. Width: About 9.7 cm. Shape: Cordate. Apex: Apiculate. Base: Cordate to reniform. Margin: Entire. Texture, upper and lower surfaces: Leathery; glabrous, smooth. Luster, upper and lower surfaces: Glossy. Venation pattern: Pinnate. Color: Developing leaves, upper surface: Between 144A and 146A. Developing leaves, lower surface: Close to 148A. Fully expanded leaves, upper surface: Darker than 137A; venation, close to 145A. Fully expanded leaves, lower surface: Between 143A and 144A; venation, close to 145A. Petiole: Length: About 24.6 cm. Diameter, just below geniculum: About 3.5 mm. Diameter, at plant base: About 5 mm. Texture, upper and lower surfaces: Smooth, glabrous; slightly glossy. Color, upper and lower surfaces: Close to 144A. Geniculum length: About 2.3 cm. Geniculum diameter: About 4 mm. Geniculum texture: Smooth, glabrous; slightly glossy. Geniculum color, upper and lower surfaces: Close to 144A. Wing length: About 2.6 cm. Wing diameter: About 4 mm. Wing color: Close to 152A to 152B flushed with close to 178C to 178D.

Inflorescence description:

*Inflorescence arrangement/habit.*—Spathes with spadices held above and beyond the foliage on strong and erect scapes. Flowering structures arise from leaf axils. Freely and continuous flowering year-round in The Netherlands. Typically about 17 inflorescences develop per plant. Inflorescences not fragrant.

*Inflorescence longevity.*—Inflorescences last about two months during the winter and last about three months during the summer; inflorescences persistent.

*Spathe.*—Length: About 8 cm. Width: About 10.4 cm. Shape: Deltoid to reniform. Apex: Abruptly acute. Base: Cordate. Margin: Entire. Texture, upper and lower surfaces: Leathery; glabrous, smooth; rugose. Luster, upper and lower surfaces: Glossy. Color: When developing, front surface: Close to 40A; towards the base, close to 41B. When developing, rear surface: Close to 42C; towards the base, flushed with close to 152D. Fully developed, front surface: Close to 40A; with development, color becoming closer to 42A and towards the base, close to 144A. Fully developed, rear surface: Close to 41B; towards the base, flushed with close to 152D.

*Spadix.*—Length: About 3.7 cm. Diameter: About 8 mm. Shape: Columnar, tapering towards the apex; apex, obtuse; base, obtuse; cross-section, rounded. Aspect: About 5° from vertical. Color: Immature: Close to 12B; towards the apex, close to 151C. Mature: Close to 11D; towards the apex, close to 15A. Flowers: Quantity per spadix: Numerous, about 200. Shape: Rounded. Height: Less than 0.5 mm. Diameter: About 2 mm. Color: Close to 155B. Pollen amount: Scarce. Pollen color: Close to 155B. Stigma shape: Ovoid. Stigma color: Close to 155D. Ovary color: Close to 155D.

*Scape.*—Length: About 35.3 cm. Diameter: About 3.5 mm. Strength: Strong. Aspect: Erect to slightly outwardly slanted to about 5° from vertical. Color: Close to 144A.

*Seed and fruit.*—Seed and fruit development has not been observed on plants of the new *Anthurium*.

Disease/pest resistance: Plants of the new *Anthurium* have not been observed to be resistant to pathogens or pests common to *Anthurium*.

Temperature tolerance: Plants of the new *Anthurium* have been observed to be tolerant to temperatures ranging from about 15° C. to about 36° C.

It is claimed:

1. A new and distinct *Anthurium* plant named 'Bardonta' as illustrated and described.

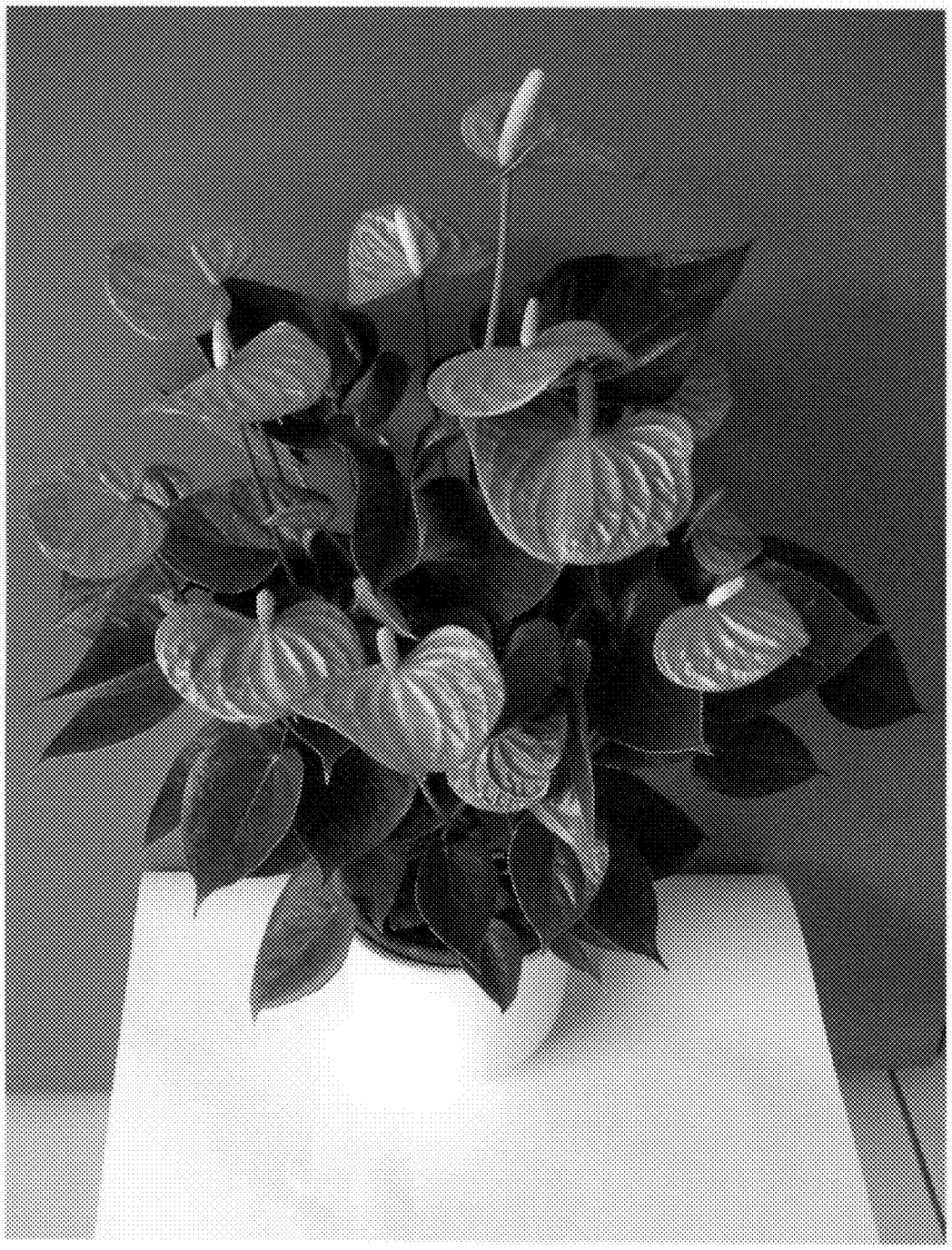

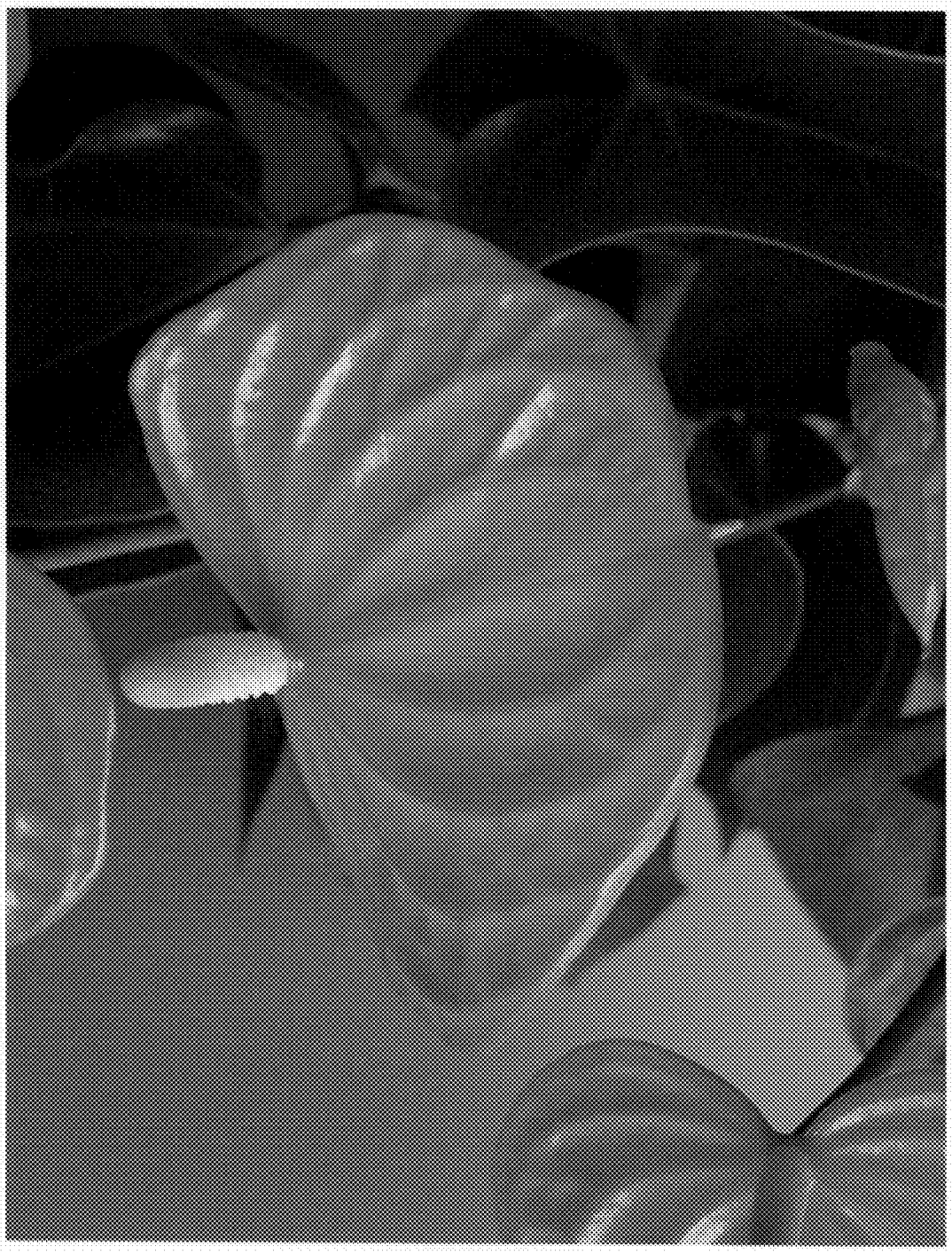

* * * * *